United States Patent
Cooper et al.

(10) Patent No.: US 7,135,435 B2
(45) Date of Patent: Nov. 14, 2006

(54) PLANT GROWTH REGULATION COMPOSITIONS AND METHODS USING GIBBERELLIN BIOSYNTHESIS INHIBITOR COMBINATIONS

(75) Inventors: Raymond B. Cooper, Hilton Head, SC (US); Roger Storey, Westfield, IN (US)

(73) Assignee: Sepro Corporation, Carmel, IN (US)

( * ) Notice: Subject to any disclaimer, the term of this patent is extended or adjusted under 35 U.S.C. 154(b) by 21 days.

(21) Appl. No.: 10/746,902

(22) Filed: Dec. 26, 2003

(65) Prior Publication Data
US 2005/0032648 A1    Feb. 10, 2005

Related U.S. Application Data

(60) Provisional application No. 60/436,909, filed on Dec. 27, 2003.

(51) Int. Cl.
| | |
|---|---|
| *A01N 37/08* | (2006.01) |
| *A01N 43/54* | (2006.01) |
| *A01N 43/653* | (2006.01) |
| *A01P 21/00* | (2006.01) |

(52) U.S. Cl. .................. 504/136; 504/139; 504/239; 504/262; 504/313

(58) Field of Classification Search ............... 504/136, 504/139, 239, 262, 313
See application file for complete search history.

(56) References Cited

U.S. PATENT DOCUMENTS 6,642,179 B1 * 11/2003 Watschke ................ 504/239

* cited by examiner

*Primary Examiner*—S. Mark Clardy
(74) *Attorney, Agent, or Firm*—Woodard, Emhardt, Moriarty, McNett & Henry LLP

(57) ABSTRACT

Described are plant growth regulation compositions and methods utilizing combinations of Class A and Class B gibberellin biosynthesis inhibitors. Preferred methods and compositions involve the combination of trinexapac-ethyl with either or both of flurprimidol and paclobutrazol, in particular to provide a synergistic effect in the regulation of the growth of turfgrass.

32 Claims, No Drawings

PLANT GROWTH REGULATION COMPOSITIONS AND METHODS USING GIBBERELLIN BIOSYNTHESIS INHIBITOR COMBINATIONS

REFERENCE TO RELATED APPLICATION

This application claims the benefit of U.S. Provisional Patent Application Ser. No. 60/436,909 filed Dec. 27, 2003, which is hereby incorporated herein by reference in its entirety.

BACKGROUND OF THE INVENTION

The present invention relates generally to plant growth regulation, and in particular to plant growth regulation utilizing combinations of active agents that each inhibit plant gibberellin biosynthesis.

As further background, agents that accelerate or retard the rate of growth of plants have been known and used in the field of turfgrass and other plant management. Agents that retard or inhibit shoot, stem and leaf elongation have traditionally been categorized by four modes of action. A first mode involves the inhibition of mitosis in the meristematic tissue which halts cell division and elongation. A second mode involves a reduction of cell elongation by inhibiting or retarding gibberellin synthesis, a plant hormone needed for cell elongation. A third mode of action involves the regulation of auxin activity and transport, and a fourth mode involves killing terminal buds and thus reducing apical dominance.

Gibberellin synthesis inhibitors are known which act at different sites in the biosynthetic pathway of gibberellins. Agents which act relatively late in the synthetic pathway are known as Class A gibberellin biosynthesis inhibitors. Trinexepac-ethyl is one such Class A agent, and is sold under the trade name Primo. Class B gibberellin biosynthesis inhibitors act relatively early in the gibberellin biosynthesis pathway. The compounds paclobutratzole and flurprimidol are known Class B gibberellin biosynthesis inhibitors and are sold under the trade names Trimmit and Cutless, respectively.

Growth regulation of turfgrass and other plants using high application rates may result in a significant waste of material, increased cost of application, and the discharge of excess plant growth regulator chemistry into the surrounding environment.

Gibberellin biosynthesis inhibitors have been used individually for some time in the management of turfgrasses such as those occurring on golf courses. Nonetheless, there remain needs for improved turfgrass and other plant management aspects which provide more effective results and/or which require lesser amounts of active agents. The present invention is addressed to these needs.

SUMMARY OF THE INVENTION

It has now been discovered that the use of gibberellin biosynthesis inhibitors in combination can provide more effective and efficient regulation of the growth of plants including turfgrass. This includes the provision of synergistic combinations of gibberellin biosynthesis inhibitors, and in particular the use of at least one Class A gibberellin biosynthesis inhibitor along with at least one Class B gibberellin biosynthesis inhibitor to achieve effective regulation of the growth of turfgrass or other plants.

In one embodiment of the invention, provided is a method for regulating the growth of a plant, and especially a turfgrass, which comprises applying to the plant a Class A gibberellin biosynthesis inhibitor and applying to the plant a Class B gibberellin biosynthesis inhibitor, especially wherein the inhibitors exhibit synergism in regulating growth of the plant. Preferred Class A gibberellin biosynthesis inhibitors are encompassed by the formula:

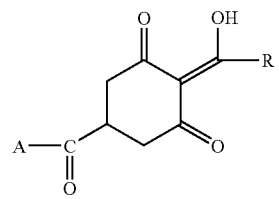

wherein

A is an $-OR_2$ or $-NR_3 R_4$ radical,

R is $C_3-C_6$ cycloalkyl, $R_2$ $R_3$ and $R_4$ are each independently hydrogen, $C_1-C_6$ alkyl, $C_1-C_6$ haloalkyl, $C_2-C_{10}$ alkoxyalkyl, $C_2-C_{10}$ alkylthioalkyl, $C_3-C_6$ alkenyl, which is unsubstituted or substituted by halogen, $C_1-C_4$ alkoxy or $C_1-C_4$ alkylthio; $C_3-C_6$ alkynyl; phenyl or $C_1-C_6$ aralkyl, wherein the phenyl nucleus is unsubstituted or substituted by halogen, $C_1-C_4$ alkyl, $C_1-C_4$ alkoxy, $C_1-C_4$ haloalkyl, nitro or cyano; one of $R_3$ and $R_4$ is methoxy; or $R_3$ and $R_4$, together with the nitrogen atom to which they are attached, form a 5- or 6-membered heterocyclic ring system which may contain an additional oxygen or sulfur atom in the ring; and the metal or ammonium salts thereof. A particularly preferred such inhibitor is trinexapac-ethyl.

Some preferred Class B gibberellin biosynthesis inhibitors are encompassed by the formula:

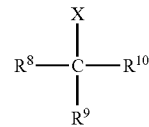

wherein $R_8$ is 2-pyrazinyl, 3-pyridyl, or 5-pyrimidinyl;

$R_9$ is phenyl, pyridyl, $C_1-C_{12}$ alkyl, or $C_3-C_8$ cycloalkyl;

$R_{10}$ is trifluoromethoxyphenyl, tetrafluoroethoxyphenyl, pentafluoroethoxyphenyl, 3,4-(difluoromethylenedioxy)phenyl, or 2,2,4,4-tetrafluoro-1,3-benzodioxanyl;

X is hydrogen, hydroxy, lower alkoxy, lower alkylthio, or lower alkanoyloxy;

or an acid addition salt thereof. A particularly preferred such inhibitor is flurprimidol. Additional Class B gibberellin biosynthesis inhibitors which may be used are encompassed by the formula:

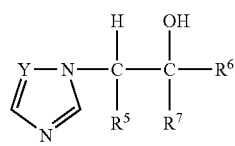

wherein
$R_5$ is alkenyl, alkynyl or optionally substituted aralkyl;
$Y$ is =N— or =CH—;
$R_6$ is cycloalkyl, alkyl or haloalkyl; and
$R_7$ is hydrogen, methyl or alkenyl, or an ester, an ether, an acid addition salt or a metal complex thereof. A particularly preferred such inhibitor is paclobutrazol.

In accordance with methods of the invention, the Class A and Class B inhibitors can be applied simultaneously to plants such as turfgrass, for example in a single tank mix; alternatively, the Class A and Class B inhibitors can be applied separately to the turfgrass or other plant, for example in rotation.

Another embodiment of the invention provides a composition for regulating plant growth that includes both a Class A gibberellin biosynthesis inhibitor and a Class B gibberellin biosynthesis inhibitor. In preferred embodiments the inhibitor combination exhibits synergism in the regulation of plant growth and especially in the regulation of turfgrass growth. Particular agents within Class A and Class B include those within the formulas noted above, and those specifically named above.

The present invention provides improved methods and compositions for regulating plant growth using combinations of gibberellin biosynthesis inhibitors. Additional embodiments as well as features and advantages of the invention will be apparent from the descriptions herein.

DETAILED DESCRIPTION OF THE PREFERRED EMBODIMENTS

For the purposes of promoting an understanding of the principles of the invention, reference will now be made to certain embodiments and specific language will be used to describe the same. It will nevertheless be understood that no limitation of the scope of the invention is thereby intended, and alterations and modifications in the illustrated device, and further applications of the principles of the invention as illustrated herein are contemplated as would normally occur to one skilled in the art to which the invention relates.

As disclosed above, the present invention provides methods and compositions for regulating plant growth that involve the use of a combination of gibberellin biosynthesis inhibitors. Particular embodiments involve the use of Class A and Class B gibberellin biosynthesis inhibitors, for example including the use of trinexapac-ethyl (4-(Cyclopropyl-alpha-hydroxymethylene)-3,5-dioxo-cyclohexanecarboxylic acid ethyl ester) as a Class A inhibitor, and the use of flurprimidol ($\alpha$-(1-methylethyl)-$\alpha$-[4-(trifluoromethoxy)phenyl]-5-pyrimidinemethanol) and/or paclobutrazol ((R*,R*)-$\beta$-[(4-chlorophenyl)methyl]-$\alpha$-(1,1-dimethylethyl)-1H-1,2,4-triazole-1-ethanol) as a Class B gibberellin biosynthesis inhibitor.

Methods and compositions of the invention employ at least one Class A gibberellin biosynthesis inhibitor. This class of inhibitors is known to those skilled in the art, and includes compounds which act at a late stage in the biosynthetic pathway of gibberellins, after the production of the first gibberellic acid compound ($GA_{12}$), for example preventing the conversion of $GA_{20}$ to $GA_1$. Trinexapac-ethyl and related compounds can be used to provide the Class A gibberellin biosynthesis inhibitor. Class A inhibitors which may be used in the invention thus are described in U.S. Pat. No. 4,693,745, and encompassed by formula:

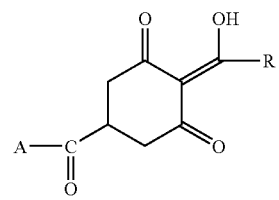

wherein
A is an —$OR_2$ or —$NR_3$, $R_4$ radical,
R is $C_3$–$C_6$ cycloalkyl,
$R_2$ $R_3$ and $R_4$ are each independently hydrogen, $C_1$–$C_6$ alkyl, $C_1$–$C_6$ haloalkyl, $C_2$–$C_{10}$ alkoxyalky, $C_2$–$C_{10}$ alkylthioalkyl; $C_3$–$C_6$ alkenyl, which is unsubstituted or substituted by halogen, $C_1$–$C_4$ alkoxy or $C_1$–$C_4$ alkylthio; $C_3$–$C_6$ alkynyl; phenyl or $C_1$–$C_6$ aralkyl, wherein the phenyl nucleus is unsubstituted or substituted by halogen, $C_1$–$C_4$ alkyl, $C_1$–$C_4$ alkoxy, $C_1$–$C_4$ haloalkyl, nitro or cyano; one of $R_3$ and $R_4$ is methoxy; or
$R_3$ and $R_4$, together with the nitrogen atom to which they are attached, form a 5- or 6-membered heterocyclic ring system which may contain an additional oxygen or sulfur atom in the ring; and the metal or ammonium salts thereof.

Trinexapac (4-(Cyclopropyl-alpha-hydroxymethylene)-3,5-dioxo-cyclohexanecarboxylic acid) and its salts or $C_1$–$C_6$ alkyl esters, including for example trinexapac-ethyl, are particularly preferred agents from this class.

Class B gibberellin biosynthesis inhibitors are also known to those skilled in the art and include compounds that act early in the biosynthetic pathway of gibberellins. For example, Class B inhibitors are known which interfere with the biosynthesis of gibberellic acid before the production of the first gibberellic acid compound, $GA_{12}$. $GA_{12}$ is not only the first GA produced but is also a precursor for all other GAs. This in effect means that GA production may be substantially slowed by the use of such Class B gibberellin biosynthesis inhibitors. A group of such inhibitors is described in U.S. Pat. No. 4,243,405, and encompassed by the formula:

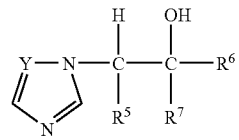

wherein
$R_5$ is alkenyl, alkynyl or optionally substituted aralkyl;
$Y$ is =N— or =CH—;
$R_6$ is cycloalkyl, alkyl or haloalkyl; and
$R_7$ is hydrogen, methyl or alkenyl., or an ester, an ether, an acid addition salt or a metal complex thereof.

Another group of Class B gibberellin biosynthesis inhibitors described in U.S. Pat. No. 4,002,628, and encompassed by the formula:

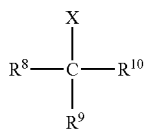

wherein $R_8$ is 2-pyrazinyl, 3-pyridyl, or 5-pyrimidinyl;

$R_9$ is phenyl, pyridyl, $C_1$–$C_{12}$ alkyl, or $C_3$–$C_8$ cycloalkyl;

$R_{10}$ is trifluoromethoxyphenyl, tetrafluoroethoxyphenyl, pentafluoroethoxyphenyl, 3,4-(difluoromethylenedioxy)phenyl, or 2,2,4,4-tetrafluoro-1,3-benzodioxanyl;

X is hydrogen, hydroxy, lower alkoxy, lower alkylthio, or lower alkanoyloxy;

or an acid addition salt thereof.

In accordance with the invention, the Class A and Class B gibberellin biosynthesis inhibitors can be used together, for example in a tank mix, or can be used separately, for example applied separately on the same date or in rotation over time. When used together, the inhibitor combination can be present in a composition in which they are combined at effective concentrations and in effective ratios to achieve plant growth regulation. Generally, the Class A and Class B plant growth regulators will be present in a molar ratio of about 1:0.625 to about 1:5 with respect to one another.

Preferably the amounts and molar ratios utilized will provide an identifiable synergism among the compounds and the regulation of plant growth, in particular in the regulation of turfgrass growth. In the case of turfgrass, this synergism may be evident in relative improvements in turf color, turf density, reduced turf scalping, growth inhibition, and/or turf quality, at any time point after application of the plant growth regulators. These turf characteristics are known and used by those skilled in the art in managing turfgrass, for example turfgrass occurring on golf courses and in particular on the fairways, putting greens and driving tees of golf courses which are maintained at relatively short lengths such as 2 inches or less, with fairways more typically being maintained at about 0.5 inch to about 1 inch, and putting greens typically being maintained at about 0.1 inch to 0.2 inch, and driving tees more typically being maintained at about 0.2 inch to 0.5 inch. In one feature of the invention, it has been discovered that the combination of a Class A and Class B inhibitor can provide a more rapid regulation of turfgrass growth and a consequent more rapid improvement in turf quality than either inhibitor applied alone at twice the rate of the combination. Thus, a decreased time interval is provided between application of the growth regulators and the achievement of substantial improvements in desirable turf characteristics.

The Class A and Class B inhibitors will be included in compositions at a level or concentration suitable for direct application to the turfgrass or other plant from conventional spraying equipment, or suitable for dilution to prepare such a composition for direct application. Plant growth regulator concentrates of the invention may for example include the Class A and Class B inhibitors each at a level of about 0.5 pounds per gallon to about 4 pounds per gallon in the case of liquid-concentrate formulations or about 25% to 80% active ingredient in the case of dry concentrate formulations. Such a concentrate can then be diluted with water or another solvent by a user for application to the turfgrass or other plant. The as-applied composition will contain the plant growth regulator(s) at a concentration or level suitable for application to the turfgrass or other plants. This may vary widely depending upon the type of spray equipment being used, and the mechanism(s) of absorption for the regulator molecule. For example, root-absorbed growth regulators such as paclobutrazol and flurprimidol are usually applied in relatively high volume spray systems, and thus can be included in as-applied liquid at relatively low concentrations. Foliar-absorbed growth regulators such as trinexapac-ethyl may be applied in relatively low volume spray systems to minimize run off from the foliage, and thus may be commonly included in the as-applied liquid at relatively higher concentrations. When applying a combination of a root-absorbed (paclobutrazol or flurprimidol) and a foliar-absorbed regulator (trinexapac-ethyl), strategies may be adopted to facilitate effective uptake of the chemicals. For example, the two growth regulators may be applied separately under conditions conducive to their mode of uptake. On the other hand, they may also be applied together while achieving suitable uptake of each. For example, in one mode of application, the root-absorbed and foliar-absorbed regulators can be applied together with a low-volume spray system, to minimize run-off and allow for the foliar uptake of the foliar-absorbed regulator. After a residence time, e.g. 0.5 to about 24 hours, the turfgrass or other plant area can then be watered, to move the root-absorbed regulator to the plant roots for absorption. These and other suitable modes of application of the growth regulator combination will be apparent to those skilled in the art given the teachings herein.

As to application rate, this will vary depending on the plant to be treated and suitable application rates for plant growth regulators are used herein or can be determined using routine experimentation. Generally, when treating turfgrass, the Class A gibberellin biosynthesis inhibitor, such as trinexapac-ethyl, will be applied at a rate about 0.02 to about 0.7 pounds of active ingredient per acre. Class B gibberellin biosynthesis inhibitors will generally be applied at a rate of about 0.05 to about 1.5 pounds of active ingredient per acre. For example, flurprimidol will typically be applied at a rate in the range of about 0.05 to about 1.5 pounds of active ingredient per acre, and paclobutrazol will typically be applied at a rate in the range of about 0.05 to about 1.0 pounds of active ingredient per acre. These rates may be used when applying the inhibitors separately (e.g. in rotation) or when applying the inhibitors together. When applying the inhibitors in rotation, it will desirable to apply the two inhibitors within about four weeks of one another, although shorter or longer times may also be used within the scope of the present invention. In one mode of operation, the two active ingredients can be applied at times and under conditions wherein effective growth regulating amounts of each are present in the plant.

Turfgrass species that can be growth regulated in accordance with the invention include, for example, warm-season species such as Bahiagrass (*Paspalum notatum*); Bermudagrass (*Cynodon dactylon*); Buffalograss (*Buchloe dactyloides*); Carpetgrass (*Axonopus affinis*); Centipedegrass (*Eremochloa ophiuroides*); Kikuyugrass (*Pennisetum cladestinum*); Seashore paspalum (*Paspalum vaginatum*); St. Augustinegrass (*Stenotaphrum secundatum*); Zoysiagrass (*Zoysia matrella* (*japonica*)); cool-season species such as Annual ryegrass (*Lolium multiflorum*); Bentgrass (*Agrostis* spp.); Fescue (*Festuca* spp.); Kentucky bluegrass (*Poa pratensis*); Perennial ryegrass (*Lolium perenne*); Bentgrass/ *Poa annua* mixtures; Kentucky bluegrass/Fescue/Ryegrass mixtures; and Kentucky bluegrass/ryegrass/*Poa annua* mixtures. Preferred turfgrasses to be controlled in the invention include Bermudagrass (*Cynodon dactylon*); Annual ryegrass (*Lolium multiflorum*); Bentgrass (*Agrostis* spp.); Kentucky bluegrass (*Poa pratensis*); and Perennial ryegrass (*Lolium perenne*).

Gibberellin biosynthesis inhibitors used in the invention can be combined with suitable liquid carriers to form liquid compositions. Any suitable carrier may be used, including those consisting essentially of water, or those including organic solvents such as alcohols, e.g. ethanol, liquid fertilizer formulations, or mixtures thereof. Water or other aqueous carriers are preferred.

Additional formulation adjuvants can be present as is conventional in the field. Typically, these will be included at levels up to about 30 percent by weight of the composition, more often at levels not exceeding about 20 percent by weight of the composition. Such adjuvants may for example include one or more surface-active agents. Potential surface active agents include the alkali, alkaline earth and ammonium salts of aromatic sulfonic acids, such as lignin-, phenol-, naphthalene-, and dibutylnaphthalenesulfonic acid, as well as those of fatty acids, alkyl and alkylaryl sulfonates, alkyllaurel ether and fatty alcohol sulfates, and salts of sulfated hexa-, hepta- and octadecanols or fatty alcohol glycol ethers, condensation products of sulfonated naphthalene and its derivatives with formaldehyde, condensation products of naphthalene or naphthalenesulfonic acids with phenol and formaldehyde, polyoxyethylene octyl phenol ether, ethoxylated isooctyl, octyl or nonylphenol, alkylphenol or tributylphenyl polyglycol ether, alkylaryl polyether alcohols, isotridecyl alcohol, fatty-alcohol ethylene oxide condensates, ethoxylated castor oil, polyoxyethylene alkyl ether or polyoxypropylene, lauryl alcohol polyglycol ether acetate, sorbitol ester, lignin sulfite waste liquors, or methylcellulose. The resulting liquid formulation may be a solution, suspension, emulsion (including microemulsions), or any other suitable form known in the art.

For the purpose of promoting a further understanding of the present invention and its features and advantages, the following specific Examples are provided. It will be understood that these Examples are illustrative, and not limiting, of the invention.

EXAMPLE 1

Tifsport Bermudagrass growing on a nursery area in South Carolina was treated with Cutless 50W (Cutless) and Primo Maxx 1EC (Primo) either singly or tank mixed to determine growth regulator activity. Cutless 50W is a commercially available product containing flurprimidol. Primo Maxx is a commercially available product containing trinexapac-ethyl. Primo was applied alone at 0.05 and 0.1 pound of active ingredient per acre (LB AI/A), Cutless was applied alone at 0.125 and 0.25 LB AI/A, and Primo+Cutless were applied at 0.05+0.125 and 0.1+0.25 LB AI/A. Plot size was 6'×12' with four replications. Three applications with a $CO_2$ back-pack sprayer were made, occurring on May 29, June 27 and July 29. Plots received approximately 0.25 inches of irrigation on each treatment date within 8 hours but not sooner than 4 hours after treatment. Ratings to evaluate performance included injury (0–10 with 0=No injury, 10=Death), color (plus or minus 100 with 100=Color of untreated, plus 100=Darker green than untreated, minus 100=Lighter green than untreated), density (DENS) (0–10 with 0=Bare ground, 10=Maximum potential density), quality (QUAL) (0–9 with 0=Poor quality, 9=Maximum potential quality), growth inhibition (GRINHIB) (percentage estimated), and scalping (CUT) (percentage estimated). The results are presented in Table 1. The following abbreviations are used in Table 1 and in the other Tables presented in these Examples: AI/A=active ingredient per acre; DAAA=Days after application; LB=pounds. Means followed by the same letter do not significantly differ (P=0.05, Duncan's New MRT).

TABLE 1

| Evaluation Date | | | | | | | 13Jun02 | 13Jun02 | 13Jun02 | 13Jun02 | 20Jun02 |
|---|---|---|---|---|---|---|---|---|---|---|---|
| Evaluation Type* | | | | | | | COLOR | DENS | QUAL | CUT | COLOR |
| Eval Unit/Scale* | | | | | | | % VISUAL | 0–10 | 0–9SCAL | % VISUAL | % VISUAL |
| Trt-Eval Interval | | | | | | | 15DAAA | SCAL | 15DAAA | 15DAAA | 22DAAA |
| Footnote No. | | | | | | | | 15DAAA | | | |
| PRM Data Type* | | | | | | | | | | | |
| Trt No | Appl Code | Treatment Name* | Form Conc | Fm Ds* | Rate | Ra Un* | Timing/ Dev Stg | | | | |
| 1 | A | PRIMO | 1 | EC | 0.05 | LB | AI/A JUNE | 117.5 ab | 9.13 ab | 8.50 a | 6.3 d | 117.5 ab |
| | A | CUTLESS | 50 | WP | 0.125 | LB | AI/A JUNE | | | | | |
| | B | PRIMO | 1 | EC | 0.05 | LB | AI/A JULY | | | | | |
| | B | CUTLESS | 50 | WP | 0.125 | LB | AI/A JULY | | | | | |
| | C | PRIMO | 1 | EC | 0.05 | LB | AI/A AUGUST | | | | | |
| | C | CUTLESS | 50 | WP | 0.125 | LB | AI/A AUGUST | | | | | |
| 2 | A | PRIMO | 1 | EC | 0.1 | LB | AI/A JUNE | 122.5 a | 9.63 a | 7.88 a | 2.5 d | 122.5 a |
| | A | CUTLESS | 50 | WP | 0.25 | LB | AI/A JUNE | | | | | |
| | B | PRIMO | 1 | EC | 0.1 | LB | AI/A JULY | | | | | |
| | B | CUTLESS | 50 | WP | 0.25 | LB | AI/A JULY | | | | | |
| | C | PRIMO | 1 | EC | 0.1 | LB | AI/A AUGUST | | | | | |
| | C | CUTLESS | 50 | WP | 0.25 | LB | AI/A AUGUST | | | | | |
| 3 | A | PRIMO | 1 | EC | 0.05 | LB | AI/A JUNE | 100.0 d | 6.88 e | 6.13 b | 57.5 a | 101.3 c |
| | B | PRIMO | 1 | EC | 0.05 | LB | AI/A JULY | | | | | |
| | C | PRIMO | 1 | EC | 0.05 | LB | AI/A AUGUST | | | | | |
| 4 | A | PRIMO | 1 | EC | 0.1 | LB | AI/A JUNE | 108.8 c | 8.00 cd | 7.50 ab | 35.0 bc | 111.3 b |
| | B | PRIMO | 1 | EC | 0.1 | LB | AI/A JULY | | | | | |
| | C | PRIMO | 1 | EC | 0.1 | LB | AI/A AUGUST | | | | | |
| 5 | A | CUTLESS | 50 | WP | 0.125 | LB | AI/A JUNE | 106.3 cd | 7.75 d | 7.38 ab | 20.0 cd | 101.3 c |
| | B | CUTLESS | 50 | WP | 0.125 | LB | AI/A JULY | | | | | |
| | C | CUTLESS | 50 | WP | 0.125 | LB | AI/A AUGUST | | | | | |

TABLE 1-continued

| Trt No | Appl Code | Treatment Name* | Form Conc | Fm Ds* | Rate | Ra Un* | Timing/ Dev Stg | | | | | |
|---|---|---|---|---|---|---|---|---|---|---|---|---|
| 6 | A | CUTLESS | 50 | WP | 0.25 | LB | AI/A JUNE | 115.0 b | 8.63 bc | 8.07 a | 11.3 d | 111.3 b |
|  | B | CUTLESS | 50 | WP | 0.25 | LB | AI/A JULY | | | | | |
|  | C | CUTLESS | 50 | WP | 0.25 | LB | AI/A AUGUST | | | | | |
| 70 |  | UNTREATED | | | | | | 100.0 d | 6.25 e | 6.00 b | 47.5 ab | 100.0 c |
| LSD (P = .05) | | | | | | | | 6.15 | 0.772 | 1.449 | 17.87 | 6.31 |
| CV | | | | | | | | 3.77 | 6.46 | 13.27 | 46.79 | 3.89 |
| Replicate F | | | | | | | | 1.526 | 0.485 | 0.077 | 1.398 | 0.923 |
| Replicate Prob (F) | | | | | | | | 0.2419 | 0.6967 | 0.9718 | 0.2757 | 0.4497 |
| Treatment F | | | | | | | | 17.601 | 21.441 | 3.836 | 12.578 | 17.176 |
| Treatment Prob (F) | | | | | | | | 0.0001 | 0.0001 | 0.0122 | 0.0001 | 0.0001 |
| Evaluation Date | | | | | | | | 20Jun02 | 20Jun02 | 27Jun02 | 27Jun02 | 27Jun02 |
| Evaluation Type* | | | | | | | | DENS | QUAL | COLOR | DENS | QUAL |
| Eval Unit/Scale* | | | | | | | | 0–10 SCAL | 0–9SCAL | % VISUAL | 0–10 SCAL | 0–9SCAL |
| Trt-Eval Interval | | | | | | | | 15DAAA | 15DAAA | 29DAAA | 29DAAA | 29DAAA |
| Footnote No. | | | | | | | | | | | | |
| PRM Data Type* | | | | | | | | | | | | |

| Trt No | Appl Code | Treatment Name* | Form Conc | Fm Ds* | Rate | Ra Un* | Timing/ Dev Stg | | | | | |
|---|---|---|---|---|---|---|---|---|---|---|---|---|
| 1 | A | PRIMO | 1 | EC | 0.05 | LB | AI/A JUNE | 9.1 ab | 8.4 a | 102.5 cd | 8.1 b | 8.0 b |
|  | A | CUTLESS | 50 | WP | 0.125 | LB | AI/A JUNE | | | | | |
|  | B | PRIMO | 1 | EC | 0.05 | LB | AI/A JULY | | | | | |
|  | B | CUTLESS | 50 | WP | 0.125 | LB | AI/A JULY | | | | | |
|  | C | PRIMO | 1 | EC | 0.05 | LB | AI/A AUGUST | | | | | |
|  | C | CUTLESS | 50 | WP | 0.125 | LB | AI/A AUGUST | | | | | |
| 2 | A | PRIMO | 1 | EC | 0.1 | LB | AI/A JUNE | 9.9 a | 8.8 a | 118.8 a | 9.6 a | 8.9 a |
|  | A | CUTLESS | 50 | WP | 0.25 | LB | AI/A JUNE | | | | | |
|  | B | PRIMO | 1 | EC | 0.1 | LB | AI/A JULY | | | | | |
|  | B | CUTLESS | 50 | WP | 0.25 | LB | AI/A JULY | | | | | |
|  | C | PRIMO | 1 | EC | 0.1 | LB | AI/A AUGUST | | | | | |
|  | C | CUTLESS | 50 | WP | 0.25 | LB | AI/A AUGUST | | | | | |
| 3 | A | PRIMO | 1 | EC | 0.05 | LB | AI/A JUNE | 7.4 d | 6.9 c | 98.8 d | 7.3 c | 7.1 d |
|  | B | PRIMO | 1 | EC | 0.05 | LB | AI/A JULY | | | | | |
|  | C | PRIMO | 1 | EC | 0.05 | LB | AI/A AUGUST | | | | | |
| 4 | A | PRIMO | 1 | EC | 0.1 | LB | AI/A JUNE | 8.4 bc | 7.8 b | 105.0 c | 8.1 b | 7.5 cd |
|  | B | PRIMO | 1 | EC | 0.1 | LB | AI/A JULY | | | | | |
|  | C | PRIMO | 1 | EC | 0.1 | LB | AI/A AUGUST | | | | | |
| 5 | A | CUTLESS | 50 | WP | 0.125 | LB | AI/A JUNE | 7.6 cd | 7.3 bc | 100.0 d | 7.3 c | 7.1 d |
|  | B | CUTLESS | 50 | WP | 0.125 | LB | AI/A JULY | | | | | |
|  | C | CUTLESS | 50 | WP | 0.125 | LB | AI/A AUGUST | | | | | |
| 6 | A | CUTLESS | 50 | WP | 0.25 | LB | AI/A JUNE | 8.4 bc | 7.6 b | 108.8 b | 8.5 b | 7.9 bc |
|  | B | CUTLESS | 50 | WP | 0.25 | LB | AI/A JULY | | | | | |
|  | C | CUTLESS | 50 | WP | 0.25 | LB | AI/A AUGUST | | | | | |
| 70 |  | UNTREATED | | | | | | 6.4 e | 6.1 d | 100.0 d | 7.3 c | 7.1 d |
| LSD (P = .05) | | | | | | | | 0.789 | 0.587 | 3.74 | 0.504 | 0.456 |
| CV | | | | | | | | 6.5 | 5.23 | 2.4 | 4.23 | 4.01 |
| Replicate F | | | | | | | | 0.877 | 4.935 | 0.891 | 3.595 | 0.853 |
| Replicate Prob (F) | | | | | | | | 0.4715 | 0.0113 | 0.4649 | 0.0340 | 0.4833 |
| Treatment F | | | | | | | | 19.056 | 20.099 | 31.313 | 26.690 | 17.842 |
| Treatment Prob (F) | | | | | | | | 0.0001 | 0.0001 | 0.0001 | 0.0001 | 0.0001 |
| Evaluation Date | | | | | | | | 09Jul02 | 09Jul02 | 09Jul02 | 09Jul02 | 29Jul02 |
| Evaluation Type* | | | | | | | | COLOR | DENS | QUAL | CUT | COLOR |
| Eval Unit/Scale* | | | | | | | | % VISUAL | 0–10 SCAL | 0–9SCAL | % VISUAL | % VISUAL |
| Trt-Eval Interval | | | | | | | | 29DAAA | 29DAAA | 29DAAA | 12DAAA | 32DAAA |

| Trt No | Appl Code | Treatment Name* | Form Conc | Fm Ds* | Rate | Ra Un* | Timing/ Dev Stg | | | | | |
|---|---|---|---|---|---|---|---|---|---|---|---|---|
| 1 | A | PRIMO | 1 | EC | 0.05 | LB | AI/A JUNE | 125.0 b | 10.0 a | 9.0 a | 0.0 c | 107.5 bc |
|  | A | CUTLESS | 50 | WP | 0.125 | LB | AI/A JUNE | | | | | |
|  | B | PRIMO | 1 | EC | 0.05 | LB | AI/A JULY | | | | | |
|  | B | CUTLESS | 50 | WP | 0.125 | LB | AI/A JULY | | | | | |
|  | C | PRIMO | 1 | EC | 0.05 | LB | AI/A AUGUST | | | | | |
|  | C | CUTLESS | 50 | WP | 0.125 | LB | AI/A AUGUST | | | | | |
| 2 | A | PRIMO | 1 | EC | 0.1 | LB | AI/A JUNE | 132.5 a | 10.0 a | 9.0 a | 0.0 c | 119.5 a |
|  | A | CUTLESS | 50 | WP | 0.25 | LB | AI/A JUNE | | | | | |
|  | B | PRIMO | 1 | EC | 0.1 | LB | AI/A JULY | | | | | |
|  | B | CUTLESS | 50 | WP | 0.25 | LB | AI/A JULY | | | | | |
|  | C | PRIMO | 1 | EC | 0.1 | LB | AI/A AUGUST | | | | | |
|  | C | CUTLESS | 50 | WP | 0.25 | LB | AI/A AUGUST | | | | | |
| 3 | A | PRIMO | 1 | EC | 0.05 | LB | AI/A JUNE | 105.0 e | 7.5 d | 7.1 d | 15.0 b | 98.8 c |
|  | B | PRIMO | 1 | EC | 0.05 | LB | AI/A JULY | | | | | |
|  | C | PRIMO | 1 | EC | 0.05 | LB | AI/A AUGUST | | | | | |

TABLE 1-continued

| Trt No | Appl Code | Treatment Name* | Form Conc | Fm Ds* | Rate | Ra Un* | Timing/ Dev Stg | | | | |
|---|---|---|---|---|---|---|---|---|---|---|---|
| 4 | A | PRIMO | 1 | EC | 0.1 | LB | AI/A JUNE | 111.3 d | 8.3 c | 7.8 c | 5.0 bc | 101.3 bc |
|  | B | PRIMO | 1 | EC | 0.1 | LB | AI/A JULY | | | | | |
|  | C | PRIMO | 1 | EC | 0.1 | LB | AI/A AUGUST | | | | | |
| 5 | A | CUTLESS | 50 | WP | 0.125 | LB | AI/A JUNE | 105.0 e | 7.5 d | 7.1 d | 7.5 bc | 100.0 c |
|  | B | CUTLESS | 50 | WP | 0.125 | LB | AI/A JULY | | | | | |
|  | C | CUTLESS | 50 | WP | 0.125 | LB | AI/A AUGUST | | | | | |
| 6 | A | CUTLESS | 50 | WP | 0.25 | LB | AI/A JUNE | 116.3 c | 8.9 b | 8.1 b | 0.0 c | 110.0 b |
|  | B | CUTLESS | 50 | WP | 0.25 | LB | AI/A JULY | | | | | |
|  | C | CUTLESS | 50 | WP | 0.25 | LB | AI/A AUGUST | | | | | |
| 70 |  | UNTREATED |  |  |  |  |  | 100.0 f | 6.5 e | 5.9 e | 40.0 | 100.0 c |
| LSD (P = .05) |  |  |  |  |  |  |  | 2.61 | 0.456 | 0.310 | 10.59 | 8.58 |
| CV |  |  |  |  |  |  |  | 1.54 | 3.67 | 2.71 | 73.91 | 5.48 |
| Replicate F |  |  |  |  |  |  |  | 0.774 | 0.853 | 1.636 | 1.383 | 1.254 |
| Replicate Prob (F) |  |  |  |  |  |  |  | 0.5235 | 0.4833 | 0.2162 | 0.2801 | 0.3197 |
| Treatment F |  |  |  |  |  |  |  | 180.484 | 74.937 | 115.364 | 16.477 | 6.880 |
| Treatment Prob (F) |  |  |  |  |  |  |  | 0.0001 | 0.0001 | 0.0001 | 0.0001 | 0.0006 |

Evaluation Date: 29Jul02, 29Jul02, 29Jul02, 29Jul02
Evaluation Type*: DENS, QUAL, GRINHIB, CUT
Eval Unit/Scale*: 0–10 SCAL, 0–9SCAL, % VISUAL, % VISUAL
Trt-Eval Interval: 32DAAA, 32DAAA, 32DAAA, 32DAAA

| Trt No | Appl Code | Treatment Name* | Form Conc | Fm Ds* | Rate | Ra Un* | Timing/ Dev Stg | | | | |
|---|---|---|---|---|---|---|---|---|---|---|---|
| 1 | A | PRIMO | 1 | EC | 0.05 | LB | AI/A JUNE | 7.6 b | 7.4 b | 13.8 b | 13.8 cd |
|  | A | CUTLESS | 50 | WP | 0.125 | LB | AI/A JUNE | | | | |
|  | B | PRIMO | 1 | EC | 0.05 | LB | AI/A JULY | | | | |
|  | B | CUTLESS | 50 | WP | 0.125 | LB | AI/A JULY | | | | |
|  | C | PRIMO | 1 | EC | 0.05 | LB | AI/A AUGUST | | | | |
|  | C | CUTLESS | 50 | WP | 0.125 | LB | AI/A AUGUST | | | | |
| 2 | A | PRIMO | 1 | EC | 0.1 | LB | AI/A JUNE | 9.5 a | 8.6 a | 28.8 a | 0.0 e |
|  | A | CUTLESS | 50 | WP | 0.25 | LB | AI/A JUNE | | | | |
|  | B | PRIMO | 1 | EC | 0.1 | LB | AI/A JULY | | | | |
|  | B | CUTLESS | 50 | WP | 0.25 | LB | AI/A JULY | | | | |
|  | C | PRIMO | 1 | EC | 0.1 | LB | AI/A AUGUST | | | | |
|  | C | CUTLESS | 50 | WP | 0.25 | LB | AI/A AUGUST | | | | |
| 3 | A | PRIMO | 1 | EC | 0.05 | LB | AI/A JUNE | 6.3 cd | 5.8 de | 0.0 d | 25.0 b |
|  | B | PRIMO | 1 | EC | 0.05 | LB | AI/A JULY | | | | |
|  | C | PRIMO | 1 | EC | 0.05 | LB | AI/A AUGUST | | | | |
| 4 | A | PRIMO | 1 | EC | 0.1 | LB | AI/A JUNE | 6.5 cd | 5.9 de | 5.0 cd | 21.3 bc |
|  | B | PRIMO | 1 | EC | 0.1 | LB | AI/A JULY | | | | |
|  | C | PRIMO | 1 | EC | 0.1 | LB | AI/A AUGUST | | | | |
| 5 | A | CUTLESS | 50 | WP | 0.125 | LB | AI/A JUNE | 7.1 bc | 6.5 cd | 3.8 cd | 11.3 cd |
|  | B | CUTLESS | 50 | WP | 0.125 | LB | AI/A JULY | | | | |
|  | C | CUTLESS | 50 | WP | 0.125 | LB | AI/A AUGUST | | | | |
| 6 | A | CUTLESS | 50 | WP | 0.25 | LB | AI/A JUNE | 7.6 b | 7.1 bc | 10.0 bc | 6.3 de |
|  | B | CUTLESS | 50 | WP | 0.25 | LB | AI/A JULY | | | | |
|  | C | CUTLESS | 50 | WP | 0.25 | LB | AI/A AUGUST | | | | |
| 70 |  | UNTREATED |  |  |  |  |  | 5.6 | 5.3 | 0.0 | 36.3 |
| LSD (P = .05) |  |  |  |  |  |  |  | 0.855 | 0.802 | 6.38 | 10.58 |
| CV |  |  |  |  |  |  |  | 8.02 | 8.13 | 49.09 | 43.82 |
| Replicate F |  |  |  |  |  |  |  | 1.042 | 0.571 | 1.339 | 3.164 |
| Replicate Prob (F) |  |  |  |  |  |  |  | 0.3979 | 0.6410 | 0.2931 | 0.0498 |
| Treatment F |  |  |  |  |  |  |  | 19.168 | 18.388 | 22.355 | 11.795 |
| Treatment Prob (F) |  |  |  |  |  |  |  | 0.0001 | 0.0001 | 0.0001 | 0.0001 |

Evaluation Date: 29Jul02, 14Aug02, 14Aug02, 14Aug02
Evaluation Type*: COLOR, DENS, QUAL, GRINHIB
Eval Unit/Scale*: % VISUAL, % VISUAL, 0–9SCAL, % VISUAL
Trt-Eval Interval: 32DAAA, 16DAAA, 16DAAA, 16DAAA

| Trt No | Appl Code | Treatment Name* | Form Conc | Fm Ds* | Rate | Ra Un* | Timing/ Dev Stg | | | | |
|---|---|---|---|---|---|---|---|---|---|---|---|
| 1 | A | PRIMO | 1 | EC | 0.05 | LB | AI/A JUNE | 125.0 a | 9.8 a | 8.8 a | 15.0 b |
|  | A | CUTLESS | 50 | WP | 0.125 | LB | AI/A JUNE | | | | |
|  | B | PRIMO | 1 | EC | 0.05 | LB | AI/A JULY | | | | |
|  | B | CUTLESS | 50 | WP | 0.125 | LB | AI/A JULY | | | | |
|  | C | PRIMO | 1 | EC | 0.05 | LB | AI/A AUGUST | | | | |
|  | C | CUTLESS | 50 | WP | 0.125 | LB | AI/A AUGUST | | | | |
| 2 | A | PRIMO | 1 | EC | 0.1 | LB | AI/A JUNE | 120.0 a | 9.1 a | 8.4 a | 21.3 a |
|  | A | CUTLESS | 50 | WP | 0.25 | LB | AI/A JUNE | | | | |
|  | B | PRIMO | 1 | EC | 0.1 | LB | AI/A JULY | | | | |
|  | B | CUTLESS | 50 | WP | 0.25 | LB | AI/A JULY | | | | |
|  | C | PRIMO | 1 | EC | 0.1 | LB | AI/A AUGUST | | | | |
|  | C | CUTLESS | 50 | WP | 0.25 | LB | AI/A AUGUST | | | | |

TABLE 1-continued

| 3 | A | PRIMO | 1 | EC | 0.05 | LB | AI/A JUNE | 103.8 bc | 7.6 b | 7.3 b | 3.8 cd |
|---|---|---|---|---|---|---|---|---|---|---|---|
|  | B | PRIMO | 1 | EC | 0.05 | LB | AI/A JULY |  |  |  |  |
|  | C | PRIMO | 1 | EC | 0.05 | LB | AI/A AUGUST |  |  |  |  |
| 4 | A | PRIMO | 1 | EC | 0.1 | LB | AI/A JUNE | 108.8 bc | 8.1 b | 7.8 b | 8.8 c |
|  | B | PRIMO | 1 | EC | 0.1 | LB | AI/A JULY |  |  |  |  |
|  | C | PRIMO | 1 | EC | 0.1 | LB | AI/A AUGUST |  |  |  |  |
| 5 | A | CUTLESS | 50 | WP | 0.125 | LB | AI/A JUNE | 105.0 bc | 7.6 b | 7.3 b | 6.3 c |
|  | B | CUTLESS | 50 | WP | 0.125 | LB | AI/A JULY |  |  |  |  |
|  | C | CUTLESS | 50 | WP | 0.125 | LB | AI/A AUGUST |  |  |  |  |
| 6 | A | CUTLESS | 50 | WP | 0.25 | LB | AI/A JUNE | 110.0 b | 8.0 b | 7.5 b | 15.0 b |
|  | B | CUTLESS | 50 | WP | 0.25 | LB | AI/A JULY |  |  |  |  |
|  | C | CUTLESS | 50 | WP | 0.25 | LB | AI/A AUGUST |  |  |  |  |
| 70 |  | UNTREATED |  |  |  |  |  | 100.0 c | 6.6 c | 6.3 c | 0.0 d |
| LSD (P = .05) |  |  |  |  |  |  |  | 10.58 | 6.12 | 0.619 | 5.58 |
| CV |  |  |  |  |  |  |  | 43.82 | 3.73 | 5.49 | 37.53 |
| Replicate F |  |  |  |  |  |  |  | 3.164 | 0.632 | 0.600 | 0.507 |
| Replicate Prob (F) |  |  |  |  |  |  |  | 0.0498 | 0.6041 | 0.6233 | 0.6824 |
| Treatment F |  |  |  |  |  |  |  | 11.795 | 19.246 | 15.446 | 15.676 |
| Treatment Prob (F) |  |  |  |  |  |  |  | 0.0001 | 0.0001 | 0.0001 | 0.0001 |

Evaluations made 13 days after the May 29 application showed significantly (P=0.05, Duncan's New MRT), better color, density and scalping reduction with Primo+Cutless tank mixed at 0.05+0.125 LB AI/A than Primo alone at 0.1 LB AI/A. There was no significant difference between Cutless applied alone at 0.25 LB AI/A and the tank mix on this observation date. By 29 days after the first application, the difference noted above had disappeared and the low rate tank mix treatment was not superior to either material applied alone at two times (2×) the respective tank mix rates.

By 12 days after the June 27 application, the low rate tank mix gave significantly better color, density and quality compared with either material applied alone at 2× the respective tank mix rates. The tank mix treatment continued to show better density, quality and overall growth inhibition compared with Primo alone at 0.1 LB AI/A 32 days after the second application. Cutless at 0.25 LB AI/A performed similar to the low rate tank mix on this date.

Ratings 16 days after the July 29 application showed that the low rate tank mix provided significantly better color, density and quality than either Cutless or Primo applied alone at 2× the respective tank mix rates.

In summary, Primo+Cutless applied to Tifsport Bermudagrass at 0.05+0.125 LB AI/A provided significantly better turf color, density and quality than either material applied alone at 2× the respective tank mix rates (Primo 0.1, Cutless 0.25 LB AI/A) in ratings made 12 to 16 days after application. Differences between tank mix and single treatments largely disappeared by 29 to 32 days after application. This trial indicates that tank mix applications of Primo+Cutless at rates substantially lower than those recommended for either material applied alone will provide good turfgrass color, density and quality, and lead to more rapid regulation and improvement of the turfgrass than either active ingredient applied alone at 2× the respective tank mix rates.

EXAMPLE 2

Tifway (419) Bermudagrass growing under fairway conditions in South Carolina was treated with Cutless 50W and Primo Maxx 1EC either singly or tank mixed to determine growth regulator activity. Primo was applied alone at 0.05 and 0.1 LB AI/A, Cutless was applied alone at 0.125 and 0.25 LB AI/A, and Primo+Cutless were applied at 0.05+ 0.125 and 0.1+0.25 LB AI/A. Plot size was 6'×12' with four replications. Three applications with a $CO_2$ back-pack sprayer were made, occurring on May 29, June 27 and July 29. Plots received approximately 0.25 inches of irrigation on each treatment date within 8 hours but not sooner than 4 hours after treatment. Ratings to evaluate performance have included injury (0–10 with 0=No injury, 10=Death), color (plus or minus 100 with 100=Color of untreated, plus 100=Darker green than untreated, minus 100=Lighter green than untreated), density (0–10 with 0=Bare ground, 10=Maximum potential density), quality (0–9 with 0=Poor quality, 9=Maximum potential quality), growth inhibition (percentage estimated), and scalping (percentage estimated). The results are presented in Table 2 below.

TABLE 2

| Evaluation Date | | | | | | | | 09Jun02 | 09Jun02 | 09Jun02 | 09Jun02 |
|---|---|---|---|---|---|---|---|---|---|---|---|
| Evaluation Type* | | | | | | | | COLOR | DENS | QUAL | CUT |
| Eval Unit/Scale* | | | | | | | | % VISUAL | 0–10SCAL | 0–9SCAL | % VISUAL |
| Trt-Eval Interval | | | | | | | | 11DAAA | 11DAAA | 11DAAA | 11DAAA |
| Trt No | Appl Code | Treatment Name* | Form Conc | Fm Ds* | Rate | Ra Un* | Timing/ Dev Stg | | | | |
| 1 | A | PRIMO | 1 | EC | 0.05 | LB | AI/A JUNE | 98.8 a | 10.00 a | 8.75 a | 0.0 a |
|  | A | CUTLESS | 50 | WP | 0.125 | LB | AI/A JUNE | | | | |
|  | B | PRIMO | 1 | EC | 0.05 | LB | AI/A JULY | | | | |
|  | B | CUTLESS | 50 | WP | 0.125 | LB | AI/A JULY | | | | |
|  | C | PRIMO | 1 | EC | 0.05 | LB | AI/A AUGUST | | | | |
|  | C | CUTLESS | 50 | WP | 0.125 | LB | AI/A AUGUST | | | | |
| 2 | A | PRIMO | 1 | EC | 0.1 | LB | AI/A JUNE | 99.0 a | 9.95 a | 8.88 a | 0.0 a |
|  | A | CUTLESS | 50 | WP | 0.25 | LB | AI/A JUNE | | | | |

TABLE 2-continued

| Trt No | Appl Code | Treatment Name* | Form Conc | Fm Ds* | Rate | Ra Un* | Timing/ Dev Stg | | | | |
|---|---|---|---|---|---|---|---|---|---|---|---|
| | B | PRIMO | 1 | EC | 0.1 | LB | AI/A JULY | | | | |
| | B | CUTLESS | 50 | WP | 0.25 | LB | AI/A JULY | | | | |
| | C | PRIMO | 1 | EC | 0.1 | LB | AI/A AUGUST | | | | |
| | C | CUTLESS | 50 | WP | 0.25 | LB | AI/A AUGUST | | | | |
| 3 | A | PRIMO | 1 | EC | 0.05 | LB | AI/A JUNE | 97.5 ab | 9.75 a | 8.68 a | 0.0 a |
| | B | PRIMO | 1 | EC | 0.05 | LB | AI/A JULY | | | | |
| | C | PRIMO | 1 | EC | 0.05 | LB | AI/A AUGUST | | | | |
| 4 | A | PRIMO | 1 | EC | 0.1 | LB | AI/A JUNE | 93.3 b | 9.75 a | 8.38 a | 0.0 a |
| | B | PRIMO | 1 | EC | 0.1 | LB | AI/A JULY | | | | |
| | C | PRIMO | 1 | EC | 0.1 | LB | AI/A AUGUST | | | | |
| 5 | A | CUTLESS | 50 | WP | 0.125 | LB | AI/A JUNE | 98.8 a | 9.70 a | 8.80 a | 0.0 a |
| | B | CUTLESS | 50 | WP | 0.125 | LB | AI/A JULY | | | | |
| | C | CUTLESS | 50 | WP | 0.125 | LB | AI/A AUGUST | | | | |
| 6 | A | CUTLESS | 50 | WP | 0.25 | LB | AI/A JUNE | 99.5 a | 9.88 a | 8.80 a | 0.0 a |
| | B | CUTLESS | 50 | WP | 0.25 | LB | AI/A JULY | | | | |
| | C | CUTLESS | 50 | WP | 0.25 | LB | AI/A AUGUST | | | | |
| 7 | | UNTREATED | | | | | | 100.0 a | 9.63 a | 8.63 a | 0.0 a |
| LSD (P = .05) | | | | | | | | 4.80 | 0.360 | 0.461 | 0.00 |
| CV | | | | | | | | 3.3 | 2.47 | 3.57 | 0.0 |
| Replicate F | | | | | | | | 0.896 | 2.990 | 0.356 | 0.000 |
| Replicate Prob (F) | | | | | | | | 0.4622 | 0.0584 | 0.7854 | 1.0000 |
| Treatment F | | | | | | | | 1.984 | 1.286 | 1.140 | 0.000 |
| Treatment Prob (F) | | | | | | | | 0.1215 | 0.3127 | 0.3794 | 1.0000 |
| Evaluation Date | | | | | | | | 14Jun02 | 14Jun02 | 14Jun02 | 14Jun02 |
| Evaluation Type* | | | | | | | | COLOR | DENS | QUAL | CUT |
| Eval Unit/Scale* | | | | | | | | % VISUAL | 0–10SCAL | 0–9SCAL | % VISUAL |
| Trt-Eval Interval | | | | | | | | 16DAAA | 16DAAA | 11DAAA | 16DAAA |

| Trt No | Appl Code | Treatment Name* | Form Conc | Fm Ds* | Rate | Ra Un* | Timing/ Dev Stg | | | | |
|---|---|---|---|---|---|---|---|---|---|---|---|
| 1 | A | PRIMO | 1 | EC | 0.05 | LB | AI/A JUNE | 116.3 a | 9.38 a | 8.70 ab | 0.0 d |
| | A | CUTLESS | 50 | WP | 0.125 | LB | AI/A JUNE | | | | |
| | B | PRIMO | 1 | EC | 0.05 | LB | AI/A JULY | | | | |
| | B | CUTLESS | 50 | WP | 0.125 | LB | AI/A JULY | | | | |
| | C | PRIMO | 1 | EC | 0.05 | LB | AI/A AUGUST | | | | |
| | C | CUTLESS | 50 | WP | 0.125 | LB | AI/A AUGUST | | | | |
| 2 | A | PRIMO | 1 | EC | 0.1 | LB | AI/A JUNE | 120.0 a | 9.50 a | 8.75 a | 1.3 cd |
| | A | CUTLESS | 50 | WP | 0.25 | LB | AI/A JUNE | | | | |
| | B | PRIMO | 1 | EC | 0.1 | LB | AI/A JULY | | | | |
| | B | CUTLESS | 50 | WP | 0.25 | LB | AI/A JULY | | | | |
| | C | PRIMO | 1 | EC | 0.1 | LB | AI/A AUGUST | | | | |
| | C | CUTLESS | 50 | WP | 0.25 | LB | AI/A AUGUST | | | | |
| 3 | A | PRIMO | 1 | EC | 0.05 | LB | AI/A JUNE | 102.5 bc | 8.38 b | 8.13 cd | 7.5 a |
| | B | PRIMO | 1 | EC | 0.05 | LB | AI/A JULY | | | | |
| | C | PRIMO | 1 | EC | 0.05 | LB | AI/A AUGUST | | | | |
| 4 | A | PRIMO | 1 | EC | 0.1 | LB | AI/A JUNE | 115.0 a | 9.00 ab | 8.38 bc | 3.8 bc |
| | B | PRIMO | 1 | EC | 0.1 | LB | AI/A JULY | | | | |
| | C | PRIMO | 1 | EC | 0.1 | LB | AI/A AUGUST | | | | |
| 5 | A | CUTLESS | 50 | WP | 0.125 | LB | AI/A JUNE | 107.5 b | 8.50 b | 8.38 bc | 6.3 ab |
| | B | CUTLESS | 50 | WP | 0.125 | LB | AI/A JULY | | | | |
| | C | CUTLESS | 50 | WP | 0.125 | LB | AI/A AUGUST | | | | |
| 6 | A | CUTLESS | 50 | WP | 0.25 | LB | AI/A JUNE | 118.8 a | 9.38 a | 8.57 ab | 0.0 d |
| | B | CUTLESS | 50 | WP | 0.25 | LB | AI/A JULY | | | | |
| | C | CUTLESS | 50 | WP | 0.25 | LB | AI/A AUGUST | | | | |
| 7 | | UNTREATED | | | | | | 100.0 c | 8.38 b | 7.88 d | 8.8 a |
| LSD (P = .05) | | | | | | | | 5.94 | 0.678 | 0.319 | 3.17 |
| CV | | | | | | | | 3.59 | 5.11 | 2.56 | 54.38 |
| Replicate F | | | | | | | | 1.043 | 9.600 | 13.807 | 1.304 |
| Replicate Prob (F) | | | | | | | | 0.3973 | 0.0005 | 0.0001 | 0.3036 |
| Treatment F | | | | | | | | 16.230 | 4.886 | 8.586 | 11.609 |
| Treatment Prob (F) | | | | | | | | 0.0001 | 0.0040 | 0.0002 | 0.0001 |
| Evaluation Date | | | | | | | | 27Jun02 | 27Jun02 | 27Jun02 | 10Jul02 |
| Evaluation Type* | | | | | | | | COLOR | DENS | QUAL | COLOR |
| Eval Unit/Scale* | | | | | | | | % VISUAL | 0–10SCAL | 0–9SCAL | % VISUAL |
| Trt-Eval Interval | | | | | | | | 29DAAA | 29DAAA | 29DAAA | 13DAAA |

| Trt No | Appl Code | Treatment Name* | Form Conc | Fm Ds* | Rate | Ra Un* | Timing/ Dev Stg | | | | |
|---|---|---|---|---|---|---|---|---|---|---|---|
| 1 | A | PRIMO | 1 | EC | 0.05 | LB | AI/A JUNE | 106.3 b | 8.13 b | 7.88 b | 116.3 b |
| | A | CUTLESS | 50 | WP | 0.125 | LB | AI/A JUNE | | | | |
| | B | PRIMO | 1 | EC | 0.05 | LB | AI/A JULY | | | | |
| | B | CUTLESS | 50 | WP | 0.125 | LB | AI/A JULY | | | | |
| | C | PRIMO | 1 | EC | 0.05 | LB | AI/A AUGUST | | | | |
| | C | CUTLESS | 50 | WP | 0.125 | LB | AI/A AUGUST | | | | |

TABLE 2-continued

| Trt No | Appl Code | Treatment Name* | Form Conc | Fm Ds* | Rate | Ra Un* | Timing/ Dev Stg | | | | |
|---|---|---|---|---|---|---|---|---|---|---|---|
| 2 | A | PRIMO | 1 | EC | 0.1 | LB | AI/A JUNE | 120.0 a | 9.50 a | 9.25 a | 121.3 a |
|  | A | CUTLESS | 50 | WP | 0.25 | LB | AI/A JUNE | | | | |
|  | B | PRIMO | 1 | EC | 0.1 | LB | AI/A JULY | | | | |
|  | B | CUTLESS | 50 | WP | 0.25 | LB | AI/A JULY | | | | |
|  | C | PRIMO | 1 | EC | 0.1 | LB | AI/A AUGUST | | | | |
|  | C | CUTLESS | 50 | WP | 0.25 | LB | AI/A AUGUST | | | | |
| 3 | A | PRIMO | 1 | EC | 0.05 | LB | AI/A JUNE | 101.3 c | 7.50 cd | 7.38 bc | 105.0 d |
|  | B | PRIMO | 1 | EC | 0.05 | LB | AI/A JULY | | | | |
|  | C | PRIMO | 1 | EC | 0.05 | LB | AI/A AUGUST | | | | |
| 4 | A | PRIMO | 1 | EC | 0.1 | LB | AI/A JUNE | 107.5 b | 8.00 bc | 7.88 b | 110.0 c |
|  | B | PRIMO | 1 | EC | 0.1 | LB | AI/A JULY | | | | |
|  | C | PRIMO | 1 | EC | 0.1 | LB | AI/A AUGUST | | | | |
| 5 | A | CUTLESS | 50 | WP | 0.125 | LB | AI/A JUNE | 100.0 c | 7.00 de | 7.13 c | 101.3 e |
|  | B | CUTLESS | 50 | WP | 0.125 | LB | AI/A JULY | | | | |
|  | C | CUTLESS | 50 | WP | 0.125 | LB | AI/A AUGUST | | | | |
| 6 | A | CUTLESS | 50 | WP | 0.25 | LB | AI/A JUNE | 108.8 b | 8.00 bc | 7.75 b | 112.5 c |
|  | B | CUTLESS | 50 | WP | 0.25 | LB | AI/A JULY | | | | |
|  | C | CUTLESS | 50 | WP | 0.25 | LB | AI/A AUGUST | | | | |
| 7 | | UNTREATED | | | | | | 100.0 c | 6.63 e | 6.25 | 100.0 e |
| LSD (P = .05) | | | | | | | | 4.58 | 0.575 | 0.521 | 3.10 |
| CV | | | | | | | | 2.9 | 4.95 | 4.59 | 1.91 |
| Replicate F | | | | | | | | 0.344 | 0.397 | 4.839 | 0.205 |
| Replicate Prob (F) | | | | | | | | 0.7940 | 0.7565 | 0.0122 | 0.8919 |
| Treatment F | | | | | | | | 21.000 | 23.066 | 27.000 | 56.727 |
| Treatment Prob (F) | | | | | | | | 0.0001 | 0.0001 | 0.0001 | 0.0001 |
| Evaluation Date | | | | | | | | 10Jul02 | 10Jul02 | 29Jul02 | 29Jul02 | 29Jul02 |
| Evaluation Type* | | | | | | | | DENS | QUAL | COLOR | DENS | QUAL |
| Eval Unit/Scale* | | | | | | | | 0–10SCAL | 0–9SCAL | % VISUAL | 0–10SCAL | 0–9SCAL |
| Trt-Eval Interval | | | | | | | | 13DAAA | 13DAAA | 32DAAA | 32DAAA | 32DAAA |

| Trt No | Appl Code | Treatment Name* | Form Conc | Fm Ds* | Rate | Ra Un* | Timing/ Dev Stg | | | | | |
|---|---|---|---|---|---|---|---|---|---|---|---|---|
| 1 | A | PRIMO | 1 | EC | 0.05 | LB | AI/A JUNE | 8.63 b | 7.88 b | 108.8 b | 8.25 b | 7.75 ab |
|  | A | CUTLESS | 50 | WP | 0.125 | LB | AI/A JUNE | | | | | |
|  | B | PRIMO | 1 | EC | 0.05 | LB | AI/A JULY | | | | | |
|  | B | CUTLESS | 50 | WP | 0.125 | LB | AI/A JULY | | | | | |
|  | C | PRIMO | 1 | EC | 0.05 | LB | AI/A AUGUST | | | | | |
|  | C | CUTLESS | 50 | WP | 0.125 | LB | AI/A AUGUST | | | | | |
| 2 | A | PRIMO | 1 | EC | 0.1 | LB | AI/A JUNE | 9.63 a | 8.63 a | 116.3 a | 9.00 a | 8.25 a |
|  | A | CUTLESS | 50 | WP | 0.25 | LB | AI/A JUNE | | | | | |
|  | B | PRIMO | 1 | EC | 0.1 | LB | AI/A JULY | | | | | |
|  | B | CUTLESS | 50 | WP | 0.25 | LB | AI/A JULY | | | | | |
|  | C | PRIMO | 1 | EC | 0.1 | LB | AI/A AUGUST | | | | | |
|  | C | CUTLESS | 50 | WP | 0.25 | LB | AI/A AUGUST | | | | | |
| 3 | A | PRIMO | 1 | EC | 0.05 | LB | AI/A JUNE | 7.38 cd | 6.88 d | 100.0 c | 7.50 c | 7.00 cd |
|  | B | PRIMO | 1 | EC | 0.05 | LB | AI/A JULY | | | | | |
|  | C | PRIMO | 1 | EC | 0.05 | LB | AI/A AUGUST | | | | | |
| 4 | A | PRIMO | 1 | EC | 0.1 | LB | AI/A JUNE | 7.38 cd | 7.13 cd | 102.5 c | 7.50 c | 7.38 bc |
|  | B | PRIMO | 1 | EC | 0.1 | LB | AI/A JULY | | | | | |
|  | C | PRIMO | 1 | EC | 0.1 | LB | AI/A AUGUST | | | | | |
| 5 | A | CUTLESS | 50 | WP | 0.125 | LB | AI/A JUNE | 7.00 de | 6.88 d | 101.3 c | 7.50 c | 7.13 cd |
|  | B | CUTLESS | 50 | WP | 0.125 | LB | AI/A JULY | | | | | |
|  | C | CUTLESS | 50 | WP | 0.125 | LB | AI/A AUGUST | | | | | |
| 6 | A | CUTLESS | 50 | WP | 0.25 | LB | AI/A JUNE | 7.88 c | 7.50 bc | 107.5 b | 8.13 b | 7.75 ab |
|  | B | CUTLESS | 50 | WP | 0.25 | LB | AI/A JULY | | | | | |
|  | C | CUTLESS | 50 | WP | 0.25 | LB | AI/A AUGUST | | | | | |
| 7 | | UNTREATED | | | | | | 6.63 | 6.25 | 100.0 c | 7.13 | 6.63 d |
| LSD (P = .05) | | | | | | | | 0.667 | 0.515 | 3.56 | 0.502 | 0.529 |
| CV | | | | | | | | 5.76 | 4.74 | 2.28 | 4.3 | 4.81 |
| Replicate F | | | | | | | | 2.483 | 4.240 | 0.155 | 0.209 | 0.070 |
| Replicate Prob (F) | | | | | | | | 0.0938 | 0.0197 | 0.9250 | 0.8890 | 0.9751 |
| Treatment F | | | | | | | | 21.177 | 20.107 | 25.138 | 14.322 | 9.469 |
| Treatment Prob (F) | | | | | | | | 0.0001 | 0.0001 | 0.0001 | 0.0001 | 0.0001 |

Evaluations 11 and 16 days after the May 29 application showed no significant differences (P=0.05, Duncan's New MRT) in color, density, quality and scalping reduction with Primo+Cutless tank mixed at 0.05+0.125 LB AI/A than with Primo or Cutless alone at 0.1 and 0.25 LB AI/A, respectively. There was no significant difference between Cutless applied alone at 0.25 LB AI/A and the tank mix on this observation date. Likewise, no differences were noted 29 days after the first applications.

By 13 days after the June 27 application, the low rate tank mix gave significantly better color, density and quality compared with Primo applied alone at 2× the tank mix rate. This tank mix rate also gave better color and density than Cutless applied alone at an 0.25 LB AI/A. Differences between the low rate tank mix and the materials applied alone at 2× the respective tank mix rates had largely disappeared by 32 days after the second application.

In summary, Primo+Cutless applied to Tifway (419) Bermudagrass at 0.05+0.125 provided significantly better turf color, density and quality than either material applied alone at 2× the respective tank mix rates (Primo 0.1, Cutless 0.25 LB AI/A) in selected ratings made 13 days after application. Differences between tank mix and single treatments largely disappeared by 29 to 32 days after application. This trial indicates that tank mix applications of Primo+Cutless at rates substantially lower than those recommended for either material applied alone will provide a relatively rapid improvement and good turfgrass color, density and quality.

EXAMPLE 3

Tifway (419) Bermudagrass growing on a nursery area in South Carolina was treated with Cutless 50W and Primo Maxx 1EC either singly or tank mixed to determine growth regulator activity. Primo was applied alone at 0.05 and 0.1 LB AI/A, Cutless was applied alone at 0.125 and 0.25 LB AI/A, and Primo+Cutless were applied at 0.05+0.125 and 0.1+0.25 LB AI/A. Plot size was 6'×12' with four replications. Two applications with a $CO_2$ back-pack sprayer were made, occurring on June 13 and July 9. Plots received approximately 0.25 inches or irrigation on each treatment date within 8 hours but not sooner than 4 hours after treatment. Ratings to evaluate performance have included injury (0–10 with 0=No injury, 10=Death), color (plus or minus 100 with 100=Color of untreated, plus 100=Darker green than untreated, minus 100=Lighter green than untreated), density (0–10 with 0=Bare ground, 10=Maximum potential density), quality (0–9 with 0=Poor quality, 9=Maximum potential quality), growth inhibition (percentage estimated), and scalping (percentage estimated). The results are presented in Table 3 below.

TABLE 3

| Evaluation Date | | | | | | | 20Jun02 | 27Jun02 | 27Jun02 | 27Jun02 | 27Jun02 |
|---|---|---|---|---|---|---|---|---|---|---|---|
| Evaluation Type* | | | | | | | COLOR | COLOR | DENS | QUAL | GRINHIB |
| Eval Unit/Scale* | | | | | | | % VISUAL | % VISUAL | 0–10SCAL | 0–9SCAL | % VISUAL |
| Trt-Eval Interval | | | | | | | 7DAAA | 14DAAA | 14DAAA | 14DAAA | 14DAAA |
| Trt No | Appl Code | Treatment Name* | Form Conc | Fm Ds* | Rate | Ra Un* | Timing/ Dev Stg | | | | |
| 1 | A | PRIMO | 1 | EC | 0.05 | LB | AI/A JUNE | 92.5 bc | 121.3 a | 9.88 a | 9.00 a | 45.0 a |
|  | A | CUTLESS | 50 | WP | 0.125 | LB | AI/A JUNE | | | | | |
|  | B | PRIMO | 1 | EC | 0.05 | LB | AI/A JULY | | | | | |
|  | B | CUTLESS | 50 | WP | 0.125 | LB | AI/A JULY | | | | | |
| 2 | A | PRIMO | 1 | EC | 0.1 | LB | AI/A JUNE | 77.5 d | 120.0 a | 9.38 ab | 8.63 a | 50.0 a |
|  | A | CUTLESS | 50 | WP | 0.25 | LB | AI/A JUNE | | | | | |
|  | B | PRIMO | 1 | EC | 0.1 | LB | AI/A JULY | | | | | |
|  | B | CUTLESS | 50 | WP | 0.25 | LB | AI/A JULY | | | | | |
| 3 | A | PRIMO | 1 | EC | 0.05 | LB | AI/A JUNE | 98.8 a | 105.0 d | 7.88 d | 7.25 c | 8.8 c |
|  | B | PRIMO | 1 | EC | 0.05 | LB | AI/A JULY | | | | | |
| 4 | A | PRIMO | 1 | EC | 0.1 | LB | AI/A JUNE | 87.5 c | 111.3 c | 8.75 bc | 8.00 b | 26.3 b |
|  | B | PRIMO | 1 | EC | 0.1 | LB | AI/A JULY | | | | | |
| 5 | A | CUTLESS | 50 | WP | 0.125 | LB | AI/A JUNE | 98.8 a | 105.0 d | 8.13 cd | 7.38 c | 11.3 c |
|  | B | CUTLESS | 50 | WP | 0.125 | LB | AI/A JULY | | | | | |
| 6 | A | CUTLESS | 50 | WP | 0.25 | LB | AI/A JUNE | 96.3 ab | 115.0 b | 8.88 b | 8.50 a | 30.0 b |
|  | B | CUTLESS | 50 | WP | 0.25 | LB | AI/A JULY | | | | | |
| 7 | | UNTREATED | | | | | | 100.0 a | 100.0 e | 6.88 e | 6.63 d | 0.0 d |
| LSD (P = .05) | | | | | | | | 5.13 | 3.59 | 0.673 | 0.495 | 6.31 |
| CV | | | | | | | | 3.71 | 2.18 | 5.31 | 4.21 | 17.37 |
| Replicate F | | | | | | | | 1.875 | 1.831 | 1.101 | 0.938 | 5.192 |
| Replicate Prob (F) | | | | | | | | 0.1700 | 0.1777 | 0.3742 | 0.4431 | 0.0093 |
| Treatment F | | | | | | | | 22.200 | 45.000 | 19.551 | 26.571 | 78.560 |
| Treatment Prob (F) | | | | | | | | 0.0001 | 0.0001 | 0.0001 | 0.0001 | 0.0001 |
| Evaluation Date | | | | | | | | 09Jul02 | 09Jul02 | 09Jul02 | 09Jul02 | |
| Evaluation Type* | | | | | | | | COLOR | DENS | QUAL | CUT | |
| Eval Unit/Scale* | | | | | | | | % VISUAL | 0–10SCAL | 0–9SCAL | % VISUAL | |
| Trt-Eval Interval | | | | | | | | 26DAAA | 26DAAA | 26DAAA | 26DAAA | |
| Trt No | Appl Code | Treatment Name* | Form Conc | Fm Ds* | Rate | Ra Un* | Timing/ Dev Stg | | | | | |
| 1 | A | PRIMO | 1 | EC | 0.05 | LB | AI/A JUNE | 118.8 b | 8.63 ab | 7.88 b | 1.3 d | |
|  | A | CUTLESS | 50 | WP | 0.125 | LB | AI/A JUNE | | | | | |
|  | B | PRIMO | 1 | EC | 0.05 | LB | AI/A JULY | | | | | |
|  | B | CUTLESS | 50 | WP | 0.125 | LB | AI/A JULY | | | | | |
| 2 | A | PRIMO | 1 | EC | 0.1 | LB | AI/A JUNE | 127.5 a | 9.50 a | 8.75 a | 0.0 d | |
|  | A | CUTLESS | 50 | WP | 0.25 | LB | AI/A JUNE | | | | | |
|  | B | PRIMO | 1 | EC | 0.1 | LB | AI/A JULY | | | | | |
|  | B | CUTLESS | 50 | WP | 0.25 | LB | AI/A JULY | | | | | |
| 3 | A | PRIMO | 1 | EC | 0.05 | LB | AI/A JUNE | 101.3 e | 6.50 c | 5.88 e | 37.5 b | |
|  | B | PRIMO | 1 | EC | 0.05 | LB | AI/A JULY | | | | | |
| 4 | A | PRIMO | 1 | EC | 0.1 | LB | AI/A JUNE | 107.5 d | 6.75 c | 6.63 cd | 21.3 c | |
|  | B | PRIMO | 1 | EC | 0.1 | LB | AI/A JULY | | | | | |

TABLE 3-continued

| Trt No | Appl Code | Treatment Name* | Form Conc | Fm Ds* | Rate | Ra Un* | Timing/ Dev Stg | | | | |
|---|---|---|---|---|---|---|---|---|---|---|---|
| 5 | A | CUTLESS | 50 | WP | 0.125 | LB | AI/A JUNE | 101.3 e | 6.63 c | 6.25 de | 41.3 b |
|   | B | CUTLESS | 50 | WP | 0.125 | LB | AI/A JULY |  |  |  |  |
| 6 | A | CUTLESS | 50 | WP | 0.25 | LB | AI/A JUNE | 112.5 c | 7.50 bc | 7.13 c | 5.0 d |
|   | B | CUTLESS | 50 | WP | 0.25 | LB | AI/A JULY |  |  |  |  |
| 7 |   | UNTREATED |  |  |  |  |  | 100.0 | 6.13 c | 4.63 f | 75.0 |
| LSD (P = .05) |  |  |  |  |  |  |  | 4.77 | 1.324 | 0.552 | 9.99 |
| CV |  |  |  |  |  |  |  | 2.92 | 12.08 | 5.52 | 25.98 |
| Replicate F |  |  |  |  |  |  |  | 3.087 | 1.691 | 1.101 | 3.809 |
| Replicate Prob (F) |  |  |  |  |  |  |  | 0.0534 | 0.2045 | 0.3745 | 0.0283 |
| Treatment F |  |  |  |  |  |  |  | 41.885 | 7.875 | 52.942 | 66.579 |
| Treatment Prob (F) |  |  |  |  |  |  |  | 0.0001 | 0.0003 | 0.0001 | 0.0001 |

| Evaluation Date |  |  |  |  |  |  |  | 29Jul02 | 29Jul02 | 29Jul02 | 29Jun02 | 29Jul02 |
|---|---|---|---|---|---|---|---|---|---|---|---|---|
| Evaluation Type* |  |  |  |  |  |  |  | COLOR | DENS | QUAL | GRINHIB | CUT |
| Eval Unit/Scale* |  |  |  |  |  |  |  | % VISUAL | 0–10SCAL | 0–9SCAL | % VISUAL | % VISUAL |
| Trt-Eval Interval |  |  |  |  |  |  |  | 20DAAB | 20DAAB | 20DAAB | 20DAAB | 20DAAB |

| Trt No | Appl Code | Treatment Name* | Form Conc | Fm Ds* | Rate | Ra Un* | Timing/ Dev Stg | | | | | |
|---|---|---|---|---|---|---|---|---|---|---|---|---|
| 1 | A | PRIMO | 1 | EC | 0.05 | LB | AI/A JUNE | 122.5 a | 8.50 a | 7.88 a | 21.3 b | 2.5 d |
|   | A | CUTLESS | 50 | WP | 0.125 | LB | AI/A JUNE |  |  |  |  |  |
|   | B | PRIMO | 1 | EC | 0.05 | LB | AI/A JULY |  |  |  |  |  |
|   | B | CUTLESS | 50 | WP | 0.125 | LB | AI/A JULY |  |  |  |  |  |
| 2 | A | PRIMO | 1 | EC | 0.1 | LB | AI/A JUNE | 120.0 a | 8.13 ab | 7.50 ab | 41.3 a | 0.0 d |
|   | A | CUTLESS | 50 | WP | 0.25 | LB | AI/A JUNE |  |  |  |  |  |
|   | B | PRIMO | 1 | EC | 0.1 | LB | AI/A JULY |  |  |  |  |  |
|   | B | CUTLESS | 50 | WP | 0.25 | LB | AI/A JULY |  |  |  |  |  |
| 3 | A | PRIMO | 1 | EC | 0.05 | LB | AI/A JUNE | 102.5 b | 6.25 d | 6.00 d | 3.8 cd | 21.3 b |
|   | B | PRIMO | 1 | EC | 0.05 | LB | AI/A JULY |  |  |  |  |  |
| 4 | A | PRIMO | 1 | EC | 0.1 | LB | AI/A JUNE | 107.5 b | 6.75 cd | 6.13 cd | 10.0 c | 15.0 bc |
|   | B | PRIMO | 1 | EC | 0.1 | LB | AI/A JULY |  |  |  |  |  |
| 5 | A | CUTLESS | 50 | WP | 0.125 | LB | AI/A JUNE | 105.0 b | 7.38 bc | 6.88 bc | 10.0 c | 11.3 c |
|   | B | CUTLESS | 50 | WP | 0.125 | LB | AI/A JULY |  |  |  |  |  |
| 6 | A | CUTLESS | 50 | WP | 0.25 | LB | AI/A JUNE | 121.3 a | 8.50 a | 7.88 a | 20.0 b | 0.0 d |
|   | B | CUTLESS | 50 | WP | 0.25 | LB | AI/A JULY |  |  |  |  |  |
| 7 |   | UNTREATED |  |  |  |  |  | 102.5 b | 5.00 e | 4.50 e | 0.0 d | 50.0 a |
| LSD (P = .05) |  |  |  |  |  |  |  | 5.56 | 0.899 | 0.755 | 7.46 | 7.98 |
| CV |  |  |  |  |  |  |  | 3.35 | 8.39 | 7.6 | 33.07 | 37.61 |
| Replicate F |  |  |  |  |  |  |  | 6.362 | 5.268 | 4.662 | 0.697 | 1.072 |
| Replicate Prob (F) |  |  |  |  |  |  |  | 0.0040 | 0.0087 | 0.0140 | 0.5660 | 0.3857 |
| Treatment F |  |  |  |  |  |  |  | 24.234 | 18.593 | 23.492 | 30.543 | 43.433 |
| Treatment Prob (F) |  |  |  |  |  |  |  | 0.0001 | 0.0001 | 0.0001 | 0.0001 | 0.0001 |

| Evaluation Date |  |  |  |  |  |  |  | 14Aug02 | 14Aug02 | 14Aug02 | 14Aug02 | 14Aug02 |
|---|---|---|---|---|---|---|---|---|---|---|---|---|
| Evaluation Type* |  |  |  |  |  |  |  | COLOR | DENS | QUAL | INJURY | GRINHIB |
| Eval Unit/Scale* |  |  |  |  |  |  |  | % VISUAL | 0–10SCAL | 0–9SCAL | 0–10SCAL | % VISUAL |
| Trt-Eval Interval |  |  |  |  |  |  |  | 36DAAB | 36DAAB | 36DAAB | 36DAAB | 36DAAB |

| Trt No | Appl Code | Treatment Name* | Form Conc | Fm Ds* | Rate | Ra Un* | Timing/ Dev Stg | | | | | |
|---|---|---|---|---|---|---|---|---|---|---|---|---|
| 1 | A | PRIMO | 1 | EC | 0.05 | LB | AI/A JUNE | 120.0 a | 8.50 a | 7.88 a | 0.00 b | 12.5 b |
|   | A | CUTLESS | 50 | WP | 0.125 | LB | AI/A JUNE |  |  |  |  |  |
|   | B | PRIMO | 1 | EC | 0.05 | LB | AI/A JULY |  |  |  |  |  |
|   | B | CUTLESS | 50 | WP | 0.125 | LB | AI/A JULY |  |  |  |  |  |
| 2 | A | PRIMO | 1 | EC | 0.1 | LB | AI/A JUNE | 115.0 ab | 7.00 c | 6.88 b | 2.63 a | 31.3 a |
|   | A | CUTLESS | 50 | WP | 0.25 | LB | AI/A JUNE |  |  |  |  |  |
|   | B | PRIMO | 1 | EC | 0.1 | LB | AI/A JULY |  |  |  |  |  |
|   | B | CUTLESS | 50 | WP | 0.25 | LB | AI/A JULY |  |  |  |  |  |
| 3 | A | PRIMO | 1 | EC | 0.05 | LB | AI/A JUNE | 105.0 cd | 7.25 c | 6.88 b | 0.00 b | 2.5 d |
|   | B | PRIMO | 1 | EC | 0.05 | LB | AI/A JULY |  |  |  |  |  |
| 4 | A | PRIMO | 1 | EC | 0.1 | LB | AI/A JUNE | 110.0 bc | 7.75 bc | 7.50 ab | 0.00 b | 8.8 bc |
|   | B | PRIMO | 1 | EC | 0.1 | LB | AI/A JULY |  |  |  |  |  |
| 5 | A | CUTLESS | 50 | WP | 0.125 | LB | AI/A JUNE | 105.0 cd | 7.38 c | 7.25 ab | 0.00 b | 3.8 cd |
|   | B | CUTLESS | 50 | WP | 0.125 | LB | AI/A JULY |  |  |  |  |  |
| 6 | A | CUTLESS | 50 | WP | 0.25 | LB | AI/A JUNE | 116.3 ab | 8.13 ab | 7.63 ab | 0.00 b | 13.8 b |
|   | B | CUTLESS | 50 | WP | 0.25 | LB | AI/A JULY |  |  |  |  |  |
| 7 |   | UNTREATED |  |  |  |  |  | 100.0 d | 6.25 d | 6.00 c | 0.00 b | 0.0 d |
| LSD (P = .05) |  |  |  |  |  |  |  | 6.89 | 0.708 | 0.783 | 0.623 | 5.77 |
| CV |  |  |  |  |  |  |  | 4.21 | 6.39 | 7.38 | 111.74 | 37.49 |
| Replicate F |  |  |  |  |  |  |  | 2.806 | 2.253 | 0.600 | 1.000 | 2.289 |
| Replicate Prob (F) |  |  |  |  |  |  |  | 0.0691 | 0.1170 | 0.6233 | 0.4155 | 0.1130 |
| Treatment F |  |  |  |  |  |  |  | 9.719 | 9.786 | 5.657 | 22.424 | 29.526 |
| Treatment Prob (F) |  |  |  |  |  |  |  | 0.0001 | 0.0001 | 0.0019 | 0.0001 | 0.0001 |

Evaluations 14 days after the June 13 application showed significantly (P=0.05, Duncan's new MRT) better color, density and overall growth inhibition with Primo+Cutless tank mixed at 0.05+0.125 LB AI/A than with Primo alone at 0.1 LB AI/A or Cutless alone at 0.25 LB AI/A. By 26 days after the first application, the low rate tank mix provided better color, density, quality and scalping reduction than Primo applied alone at 0.1 LB AI/A. Cutless applied alone at 0.25 LB AI/A was not significantly different from the low rate tank mix with any of the evaluation criteria.

By 20 days after the second application made July 9, the low rate tank mix gave significantly better color, density, quality, overall growth inhibition and scalping reduction than Primo applied alone at 0.1 LB AI/A. Ratings made 36 days after the second application showed few, if any, significant differences between the low rate tank mix and either material applied alone at 2× the respective tank mix rate.

In summary, Primo+Cutless applied to Tifway (419) Bermudagrass at 0.05+0.125 provided significantly better turf color, density and quality than either material applied alone at 2× the respective tank mix rates (Primo 0.1, Cutless 0.25 LB AI/A) in ratings made 14 to 20 days after application. Differences between tank mix and single treatments largely disappeared by 26 to 36 days after application. This trial indicates that tank mix applications of Primo+Cutless at rates substantially lower than those recommended for either material applied alone will provide a relatively rapid regulation and good turfgrass color, density and quality.

EXAMPLE 4

The general procedure of Example 1 was repeated, except adding to the protocol testing of combinations of paclobutrazol and trinexepac-ethyl. The application regimen for each plot is outlined below.

| Plot | PGR regimen |
|------|-------------|
| 1 | Primo + Cutless 0.05 + 0.125 lb AI/A |
| 2 | Primo + TGR 0.05 + 0.125 lb AI/A |
| 3 | Primo 0.05 lb AI/A |
| 4 | Primo 0.1 lb AI/A |
| 5 | Cutless 0.125 lb AI/A |
| 6 | Cutless 0.25 lb AI/A |
| 7 | TGR 0.125 lb AI/A |
| 8 | TGR 0.25 lb AI/A |
| 9 | Untreated (check) |

Applications were made on August 20. The results evidenced that surprisingly beneficial treatments of turfgrass were achieved through combinations of trinexapac-ethyl with paclobutrazol and with flurprimidol, in a fashion similar- to Examples 1–3 above.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all patents and other publications cited herein are hereby incorporated by reference in their entirety as if each had been individually incorporated by reference and fully set forth.

What is claimed is:

1. A method for regulating plant growth, comprising:
    applying to a plant a Class A gibberellin biosynthesis inhibitor; and
    applying to the plant a Class B gibberellin biosynthesis inhibitor;
    wherein said Class A and Class B gibberellin synthesis inhibitors exhibit synergism in regulating growth of the plant.

2. A method according to claim 1, wherein:
    said Class A gibberellin synthesis inhibitor is encompassed by the formula:

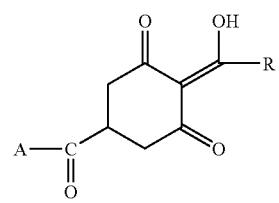

wherein
A is an —OR$_2$ or —NR$_3$ R$_4$ radical,
R is C$_3$–C$_6$ cycloalkyl,
R$_2$ R$_3$ and R$_4$ are each independently hydrogen, C$_1$–C$_6$ alkyl, C$_1$–C$_6$ haloalkyl, C$_2$–C$_{10}$ alkoxyalkyl, C$_2$–C$_{10}$ alkylthioalkyl, C$_3$–C$_6$ alkenyl, which is unsubstituted or substituted by halogen, C$_1$–C$_4$ alkoxy or C$_1$–C$_4$ alkylthio; C$_3$–C$_6$ alkynyl; phenyl or C$_1$–C$_6$ aralkyl, wherein the phenyl nucleus is unsubstituted or substituted by halogen, C$_1$–C$_4$ alkyl, C$_1$–C$_4$ alkoxy, C$_1$–C$_4$ haloalkyl, nitro or cyano; one of R$_3$ and R$_4$ is methoxy; or
R$_3$ and R$_4$, together with the nitrogen atom to which they are attached, form a 5- or 6-membered heterocyclic ring system which may contain an additional oxygen or sulfur atom in the ring; and the metal or ammonium salts thereof.

3. A method according to claim 2, wherein the Class A gibberellin synthesis inhibitor is trinexapac-ethyl.

4. A method according to claim 1, wherein the Class B gibberellin synthesis inhibitor is encompassed by the formula:

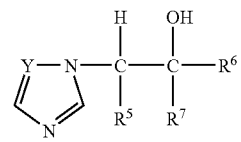

wherein
R$_5$ is alkenyl, alkynyl or optionally substituted aralkyl;
Y is =N— or =CH—;
R$_6$ is cycloalkyl, alkyl or haloalkyl; and
R$_7$ is hydrogen, methyl or alkenyl, or an ester, an ether, an acid addition salt or a metal complex thereof.

5. A method according to claim 4, wherein the Class B gibberellin synthesis inhibitor is paclobutrazol.

6. A method according to claim 1, wherein:
    the Class B gibberellin synthesis inhibitor is encompassed by the formula:

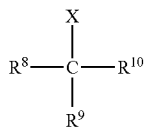

wherein
$R_8$ is 2-pyrazinyl, 3-pyridyl, or 5-pyrimidinyl;
$R_9$ is phenyl, pyridyl, $C_1$–$C_{12}$ alkyl, or $C_3$–$C_8$ cycloalkyl;
$R_{10}$ is trifluoromethoxyphenyl, tetrafluoroethoxyphenyl, pentafluoroethoxyphenyl, 3,4-(difluoromethylenedioxy)phenyl, or 2,2,4,4-tetrafluoro-1,3-benzodioxanyl;
X is hydrogen, hydroxy, lower alkoxy, lower alkylthio, or lower alkanoyloxy;
or an acid addition salt thereof.

7. A method according to claim 6, wherein the Class B gibberellin synthesis inhibitor is flurprimidol.

8. A method according to any of claims 1–7, wherein the Class A and Class B gibberellin biosynthesis inhibitors are applied together.

9. A method according any of claims 1–7, wherein the Class A and Class B gibberellin biosynthesis inhibitors are applied separatetly.

10. A method according to claim 1, wherein the plant is turfgrass.

11. A method according to claim 10, wherein the Class A gibberellin biosynthesis inhibitor is trinexepac-ethyl, and wherein the trinexepac-ethyl is applied at a level of about 0.02 to about 0.7 pounds of active ingredient per acre.

12. A method according to claim 11, wherein the Class B gibberellin biosynthesis inhibitor is flurprimidol, and wherein the flurprimidol is applied at a level of about 0.05 to about 1.5 pounds of active ingredient per acre.

13. A method according to claim 11, wherein the Class B gibberellin biosynthesis inhibitor is paclobutrazol, and wherein the paclobutrazol is applied at a level of about 0.05 to 1.0 pounds of active ingredient per acre.

14. A method according to any of claims 10–13, wherein the Class A and Class B gibberellin biosynthesis inhibitors are applied together.

15. A method according to any of claims 10–13, wherein the Class A and Class B gibberellin biosynthesis inhibitors are applied separately.

16. A method according to claim 14, wherein the turfgrass comprises one or more grasses selected from as Bahiagrass (*Paspalum notatum*); Bermudagrass (*Cynodon dactylon*); Buffalograss (*Buchloe dactyloides*); Carpetgrass (*Axonopus affinis*); Centipedegrass (*Eremochloa ophiuroides*); Kikuyugrass (*Pennisetum cladestinum*); Seashore paspalum (*Paspalum vaginatum*); St. Augustinegrass (*Stenotaphrum secundatum*); Zoysiagrass (*Zoysia matrella (japonica)*); Annual ryegrass (*Lolium multiflorum*); Bentgrass (*Agrostis* spp.); Fescue (*Festuca* spp.); Kentucky bluegrass (*Poa pratensis*); Perennial ryegrass (*Lolium perenne*); and *Poa annua*.

17. A method according to claim 14, wherein the turfgrass comprises one or more grasses selected from Bermudagrass (*Cynodon dactylon*); Annual ryegrass (*Lolium multiflorum*); Bentgrass (*Agrostis* spp.); Kentucky bluegrass (*Poa pratensis*); and Perennial ryegrass (*Lolium perenne*).

18. A composition for regulating plant growth, comprising:
a Class A gibberellin biosynthesis inhibitor; and
a Class B gibberellin biosynthesis inhibitor;
wherein said biosynthesis inhibitors exhibit synergism in the regulation of plant growth.

19. A composition according to claim 18, wherein:
said Class A gibberellin synthesis inhibitor is encompassed by the formula:

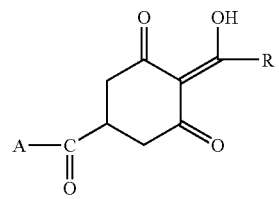

wherein
A is an —$OR_2$ or —$NR_3$, $R_4$ radical,
R is $C_3$–$C_6$ cycloalkyl,
$R_2$, $R_3$ and $R_4$ are each independently hydrogen, $C_1$–$C_6$ alkyl, $C_1$–$C_6$ haloalkyl, $C_2$–$C_{10}$ alkoxyalkyl, $C_2$–$C_{10}$ alkylthioalkyl, $C_3$–$C_6$ alkenyl, which is unsubstituted or substituted by halogen, $C_1$–$C_4$ alkoxy or $C_1$–$C_4$ alkylthio; $C_3$–$C_6$ alkynyl; phenyl or $C_1$–$C_6$ aralkyl, wherein the phenyl nucleus is unsubstituted or substituted by halogen, $C_1$–$C_4$ alkyl, $C_1$–$C_4$ alkoxy, $C_1$–$C_4$ haloalkyl, nitro or cyano; one of $R_3$ and $R_4$ is methoxy; or
$R_3$ and $R_4$, together with the nitrogen atom to which they are attached, form a 5- or 6-membered heterocyclic ring system which may contain an additional oxygen or sulfur atom in the ring; and the metal or ammonium salts thereof.

20. A composition according to claim 18, wherein the Class A gibberellin synthesis inhibitor is trinexapac-ethyl.

21. A composition according to claim 18, wherein the Class B gibberellin synthesis inhibitor is encompassed by the formula:

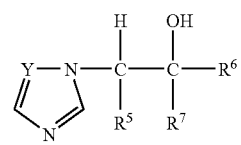

wherein
$R_5$ is alkenyl, alkynyl or optionally substituted aralkyl;
Y is =N— or =CH—;
$R_6$ is cycloalkyl, alkyl or haloalkyl; and
$R_7$ is hydrogen, methyl or alkenyl, or an ester, an ether, an acid addition salt or a metal complex thereof.

22. A composition according to claim 21, wherein the Class B gibberellin synthesis inhibitor is paclobutrazol.

23. A composition according to claim 18, wherein:
the Class B gibberellin synthesis inhibitor is encompassed by the formula:

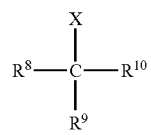

wherein
R$_8$ is 2-pyrazinyl, 3-pyridyl, or 5-pyrimidinyl;
R$_9$ is phenyl, pyridyl, C$_1$–C$_{12}$ alkyl, or C$_3$–C$_8$ cycloalkyl;
R$_{10}$ is trifluoromethoxyphenyl, tetrafluoroethoxyphenyl, pentafluoroethoxyphenyl, 3,4-(difluoromethylenedioxy)phenyl, or 2,2,4,4-tetrafluoro-1,3-benzodioxanyl;
X is hydrogen, hydroxy, lower alkoxy, lower alkylthio, or lower alkanoyloxy;
or an acid addition salt thereof.

24. A composition according to claim 23, wherein the Class B gibberellin synthesis inhibitor is flurprimidol.

25. A composition according to claim 18, wherein:
the Class A gibberellin biosynthesis inhibitor is trinexepac-ethyl, and wherein the trinexepac-ethyl is present in the composition at a concentration of about 0.5 to about 3 pounds per gallon.

26. A composition according to claim 18, wherein:
the Class B gibberellin biosynthesis inhibitor is flurprimidol, and wherein the flurprimidol is present in the composition at a concentration of about 0.5 to about 3 pounds per gallon.

27. A composition according to claim 18, wherein:
the Class B gibberellin biosynthesis inhibitor is paclobutrazol, and wherein the paclobutrazol is present in the composition at a level of about 0.5 to about 3 pounds per gallon.

28. A composition according to claim 26, adapted for application to turfgrass.

29. A composition according to claim 27, adapted for application to turfgrass.

30. A method according to claim 28 or 29, wherein the turfgrass comprises one or more grasses selected from Bermudagrass (*Cynodon dactylon*); Annual ryegrass (*Lolium multiflorum*); Bentgrass (*Agrostis* spp.); Kentucky bluegrass (*Poa pratensis*); and Perennial ryegrass (*Lolium perenne*).

31. A composition according to claim 18, which comprises an aqueous carrier.

32. A composition according to claim 18, wherein the Class A and Class B gibberellin biosynthesis inhibitors are present in a molar ratio of about 1:0.625 to about 1:5.

* * * * *

(12) INTER PARTES REEXAMINATION CERTIFICATE (0345th)
United States Patent
Cooper et al.

(10) Number: US 7,135,435 C1
(45) Certificate Issued: Feb. 14, 2012

(54) PLANT GROWTH REGULATION COMPOSITIONS AND METHODS USING GIBBERELLIN BIOSYNTHESIS INHIBITOR COMBINATIONS

(75) Inventors: Raymond B. Cooper, Hilton Head, SC (US); Roger Storey, Westfield, IN (US)

(73) Assignee: Sepro Corporation, Carmel, IN (US)

Reexamination Request:
No. 95/001,356, May 17, 2010

Reexamination Certificate for:
Patent No.: 7,135,435
Issued: Nov. 14, 2006
Appl. No.: 10/746,902
Filed: Dec. 26, 2003

Related U.S. Application Data

(60) Provisional application No. 60/436,909, filed on Dec. 27, 2003.

(51) Int. Cl.
*A01N 37/08* (2006.01)
*A01N 37/42* (2006.01)
*A01N 43/54* (2006.01)
*A01N 43/653* (2006.01)
*A01N 47/28* (2006.01)
*A01N 61/00* (2006.01)
*A01P 21/00* (2006.01)

(52) U.S. Cl. .......................... 504/136; 504/139; 504/239; 504/262; 504/313

(58) Field of Classification Search ........................ None
See application file for complete search history.

(56) References Cited

To view the complete listing of prior art documents cited during the proceeding for Reexamination Control Number 95/001,356, please refer to the USPTO's public Patent Application Information Retrieval (PAIR) system under the Display References tab.

*Primary Examiner* — Bruce Campell

(57) ABSTRACT

Described are plant growth regulation compositions and methods utilizing combinations of Class A and Class B gibberellin biosynthesis inhibitors. Preferred methods and compositions involve the combination of trinexapac-ethyl with either or both of flurprimidol and paclobutrazol, in particular to provide a synergistic effect in the regulation of the growth of turfgrass.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-32 are cancelled.

* * * * *